United States Patent
Diaz

(10) Patent No.: US 7,163,552 B2
(45) Date of Patent: Jan. 16, 2007

(54) STENT DELIVERY SYSTEM WITH HYDRAULIC DEPLOYMENT

(75) Inventor: Juan-Carlos Diaz, Miami, FL (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 406 days.

(21) Appl. No.: 09/978,243

(22) Filed: Oct. 15, 2001

(65) Prior Publication Data

US 2002/0045929 A1   Apr. 18, 2002

Related U.S. Application Data

(60) Provisional application No. 60/240,308, filed on Oct. 13, 2000.

(51) Int. Cl.
*A61F 2/82* (2006.01)

(52) U.S. Cl. ................... 623/1.12

(58) Field of Classification Search ........ 623/1.12, 623/1.11; 606/108
See application file for complete search history.

(56) References Cited

U.S. PATENT DOCUMENTS

| | | | |
|---|---|---|---|
| 5,240,537 A * | 8/1993 | Bodicky ............... 156/244.13 |
| 5,326,011 A * | 7/1994 | Mager et al. ............ 226/181 |
| 5,445,646 A | 8/1995 | Euteneuer et al. |
| 5,571,135 A | 11/1996 | Fraser et al. |
| 5,709,703 A * | 1/1998 | Lukic et al. ............ 623/1.12 |
| 5,772,669 A | 6/1998 | Vrba |
| 5,817,101 A | 10/1998 | Fiedler |
| 5,924,664 A * | 7/1999 | Mileos et al. ......... 248/281.11 |
| 5,957,930 A | 9/1999 | Vrba |
| 6,004,328 A | 12/1999 | Solar |
| 6,019,778 A | 2/2000 | Wilson et al. |
| 6,056,759 A | 5/2000 | Fiedler |
| 6,113,608 A | 9/2000 | Monroe et al. |
| 6,206,888 B1 | 3/2001 | Bicek et al. |
| 6,254,612 B1 | 7/2001 | Hieshima |
| 6,254,628 B1 | 7/2001 | Wallace et al. |
| 6,368,344 B1 * | 4/2002 | Fitz ..................... 623/1.11 |
| 6,514,261 B1 * | 2/2003 | Randall et al. ............ 606/108 |
| 2001/0034549 A1 * | 10/2001 | Bartholf et al. .......... 623/1.12 |
| 2003/0050686 A1 * | 3/2003 | Raeder-Devens et al. .. 623/1.11 |

FOREIGN PATENT DOCUMENTS

| | | |
|---|---|---|
| EP | 0607468 A1 | 12/1992 |
| EP | 0 705 578 A1 | 10/1996 |
| WO | WO 00/18330 | 4/2000 |

* cited by examiner

*Primary Examiner*—Michael Thaler

(57) ABSTRACT

A hydraulic stent and stent graft delivery system utilizing at least two different structural materials to effectuate the easy retention and release of the stent and stent graft, while maintaining structural and sealing integrity for a pressurizable fluid chamber. An anti kinking spacer is disclosed which prevents buckling/kinking of the otherwise unsupported sheath containment section when the catheter assembly is bent such as for insertion a movement to the delivery site. A configuration according to the invention provides a flexible small or dual diameter delivery system that uses fluid pressure within the catheter to retract the stent/stent graft containment sheath and allow the delivery and deployment of the stent/stent graft.

29 Claims, 6 Drawing Sheets

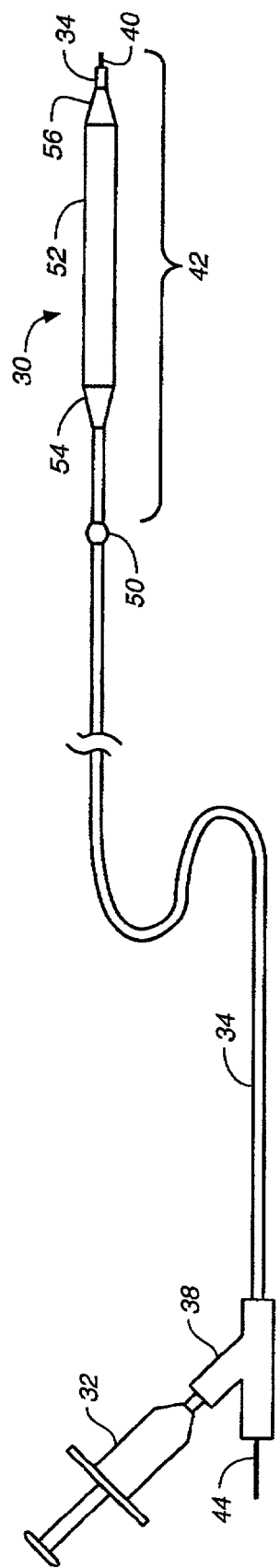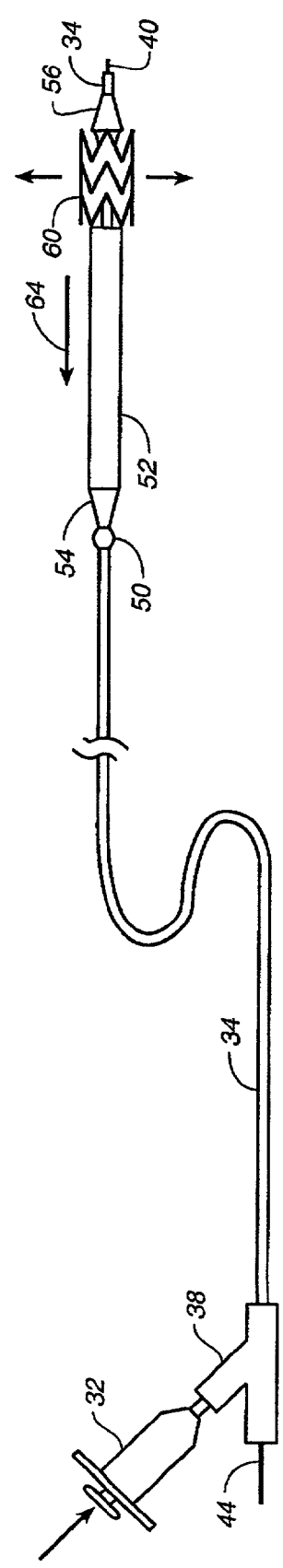

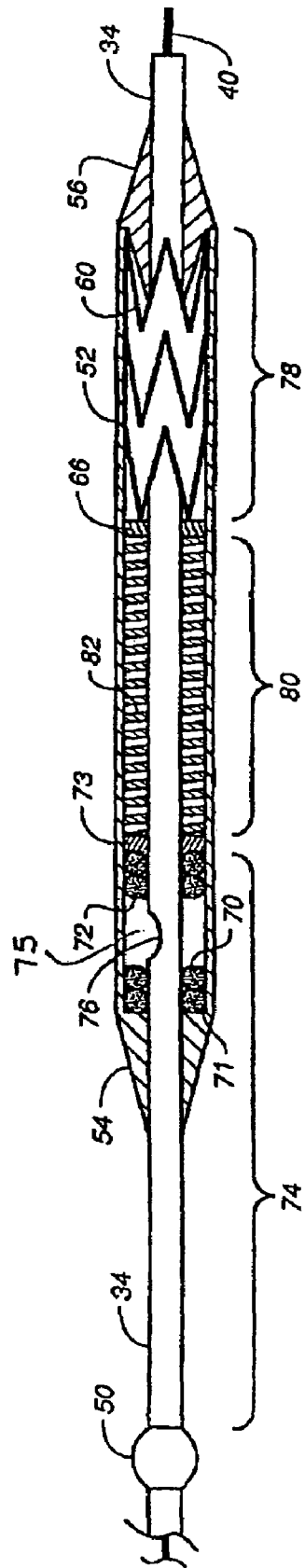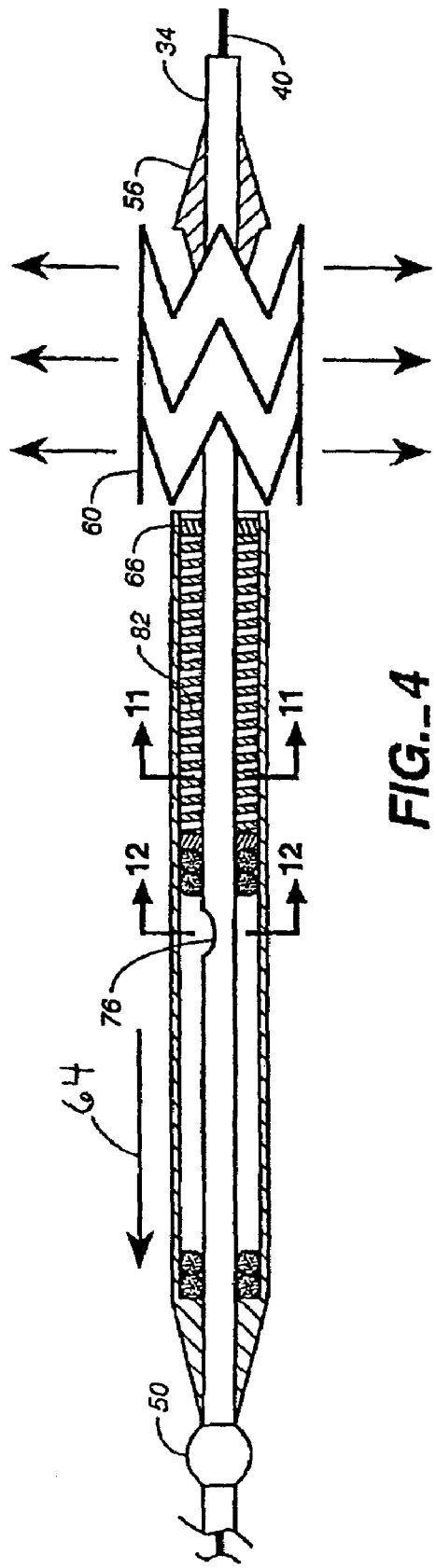
FIG._3
FIG._4

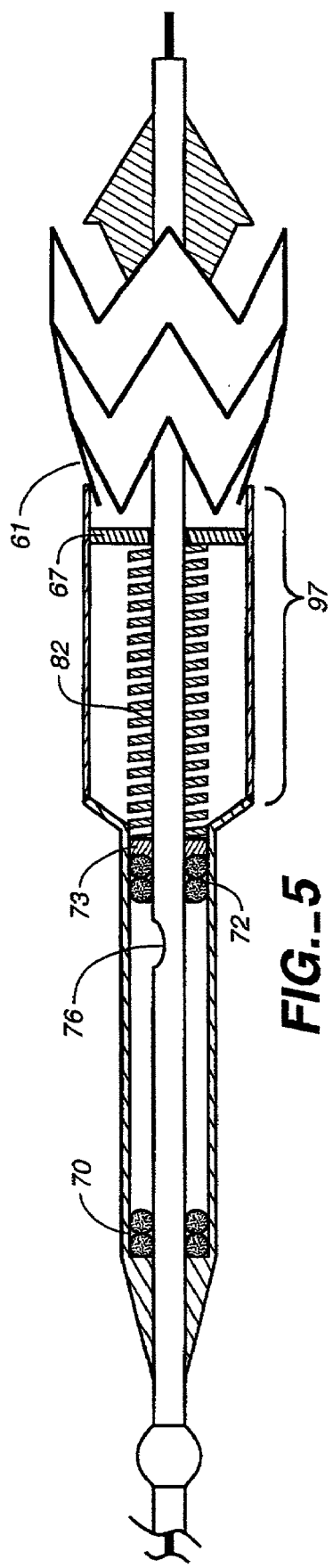
FIG._5
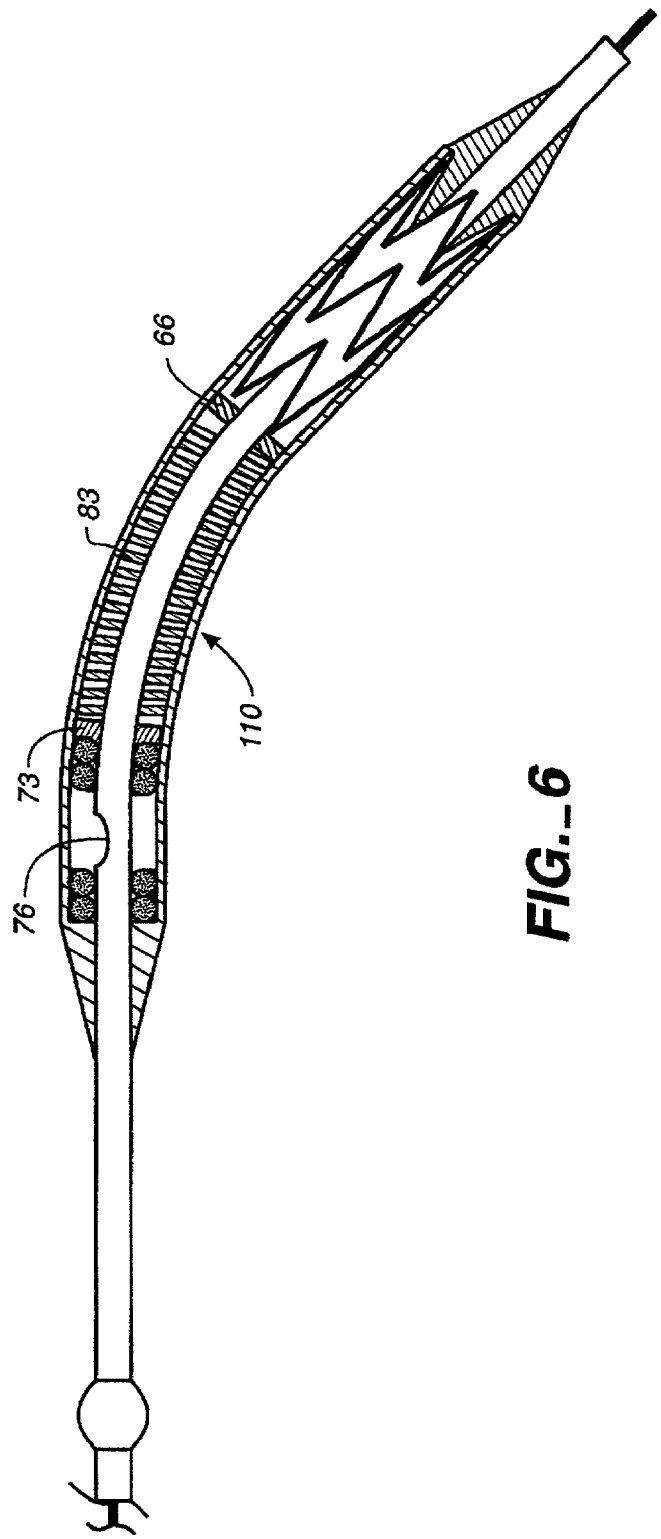
FIG._6

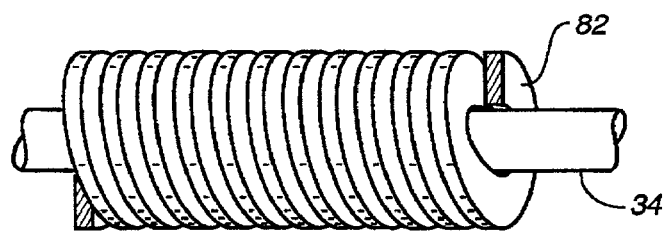
FIG._7
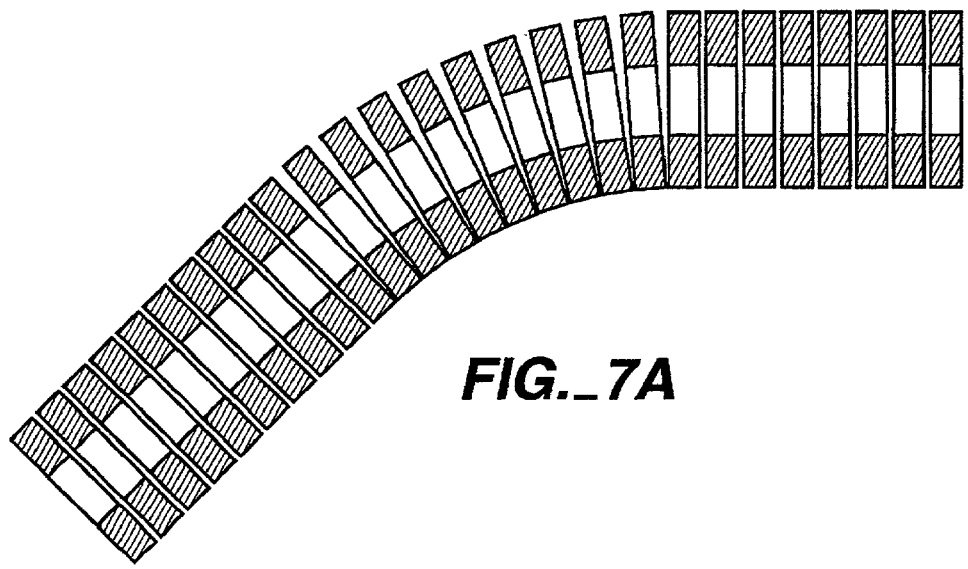
FIG._7A
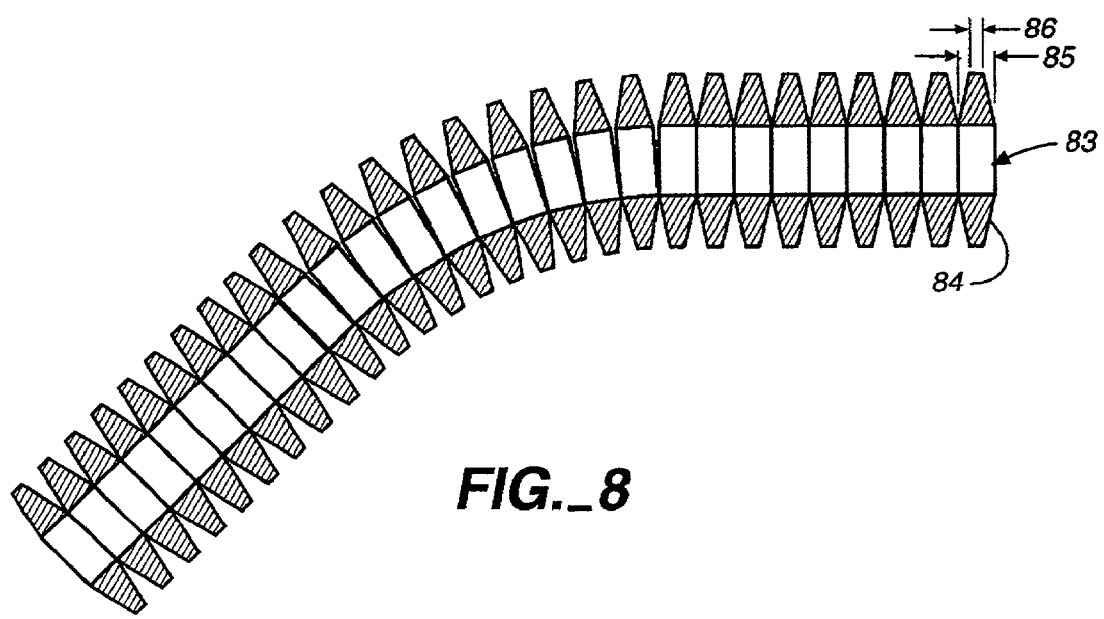
FIG._8

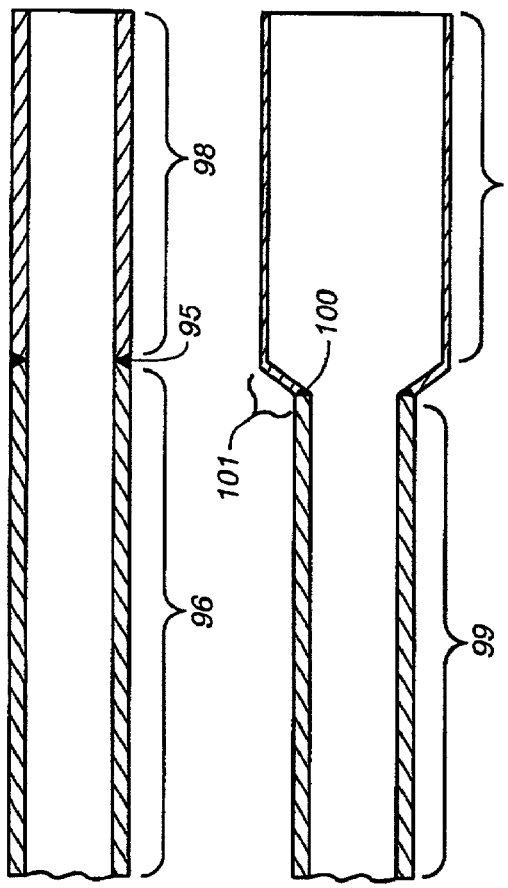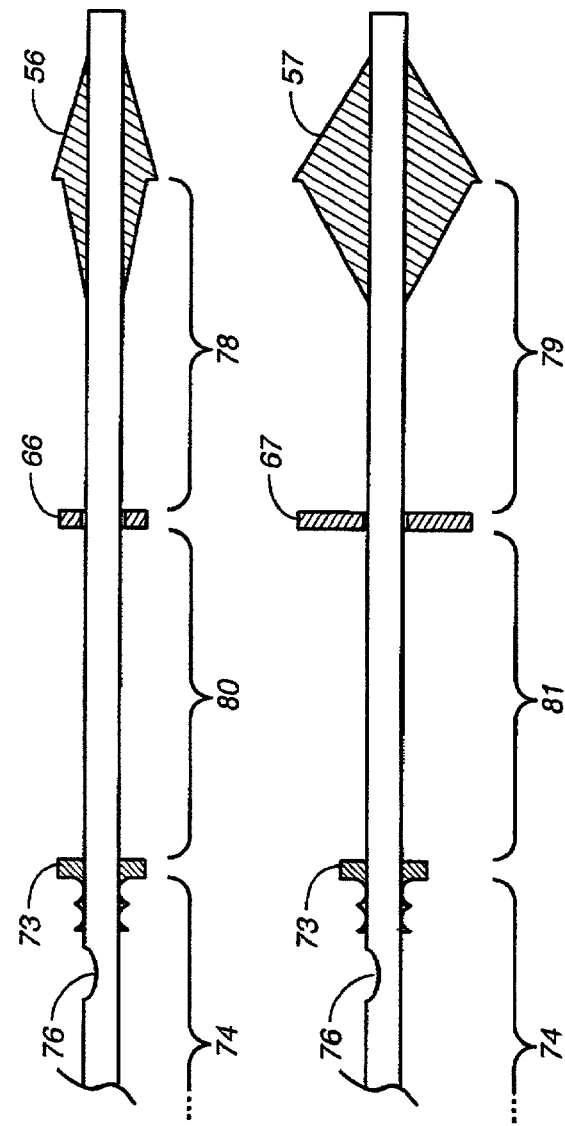

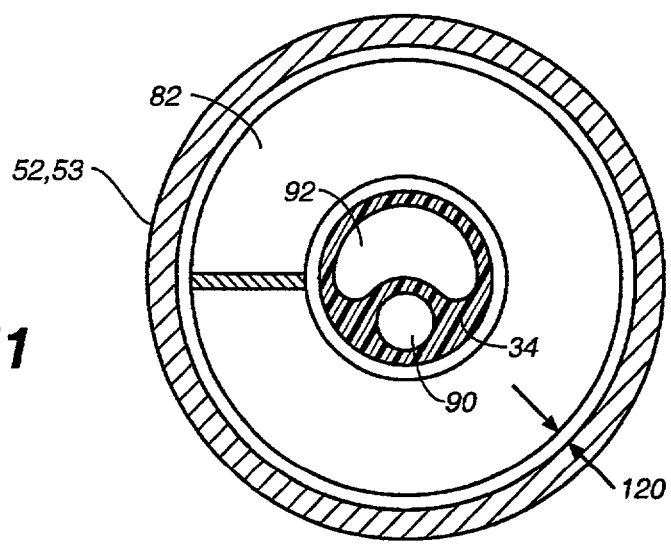
FIG._11
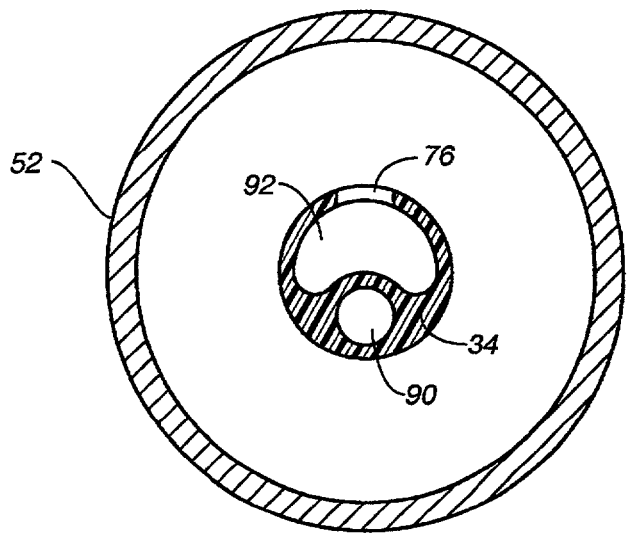
FIG._12
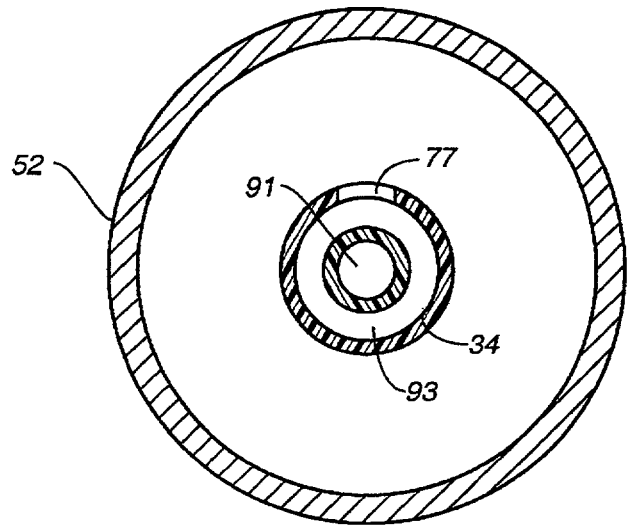
FIG._13

STENT DELIVERY SYSTEM WITH HYDRAULIC DEPLOYMENT

PRIORITY CLAIM

This application is a continuation in part application claiming priority from U.S. Provisional Patent Application No. 60/240,308, filed on Oct. 13, 2000.

FIELD OF THE INVENTION

This invention relates to the field of stents, and more particularly to the field of the delivery and deployment of self-expanding stent grafts.

BACKGROUND TO THE INVENTION

The aorta is the main artery of the body, arising from the base of the left ventricle of the heart. It is a large vessel, about one inch in diameter, with thick, elastic walls to withstand the changes in pressure as the heart beats. It supplies oxygenated blood to all arteries except the pulmonary artery (which carries blood to the lungs to be oxygenated). The aorta curves behind the heart and down the chest into the abdomen, where it divides into the two iliac arteries.

A pathologic dilation or balloon like enlargement of the aorta below the renal arteries may occur as a consequence of aging, atherosclerosis, infection, inflammation, trauma, congenital anomalies, or other pathologic conditions. Localized dilation of the aorta below the renal arteries to a diameter 50 percent greater than the expected normal diameter is known as abdominal aortic aneurysm, or AAA. Generally, aneurysms grow gradually over time, increasing by an average of two to three millimeters annually. It can take 10 to 15 years for an aneurysm to reach a size at which surgery is deemed necessary. Surgical repair of abdominal aortic aneurysm is indicated when the risk of rupture is believed to exceed the risk associated with open surgery. The risk of rupture increases with the size of the aneurysm. Due to the high risk of rupture for abdominal aortic aneurysms greater than 5 cm and the mortality associated with rupture, surgical repair of such aneurysms is the standard of care. At 5 to 6 cm, the risk of rupture increases by 20 percent per year.

Abdominal aortic aneurysm is the 13th leading cause of death in the United States accounting for more than 16,000 deaths annually. More than 40,000 procedures to treat abdominal aortic aneurysms are performed in the United States annually with approximately 32,000 new patients diagnosed with unruptured aneurysms each year. Of those diagnosed patients, 24,000 were over the age of 65. More than two million people are estimated to have an undiagnosed abdominal aortic aneurysm. Over the past 40 years, the prevalence of abdominal aortic aneurysm has risen three-fold.

Studies indicate that for aneurysms larger than 4 cm, there is a 3 to 4 percent prevalence in men age 65 to 80 and as high as 12 percent in elderly males with high blood pressure.

Generally, abdominal aortic aneurysms are asymptomatic and are often discovered only as a result of investigation of other medical problems. The primary risk posed by an abdominal aortic aneurysm is its propensity to rupture. Emergent surgical repair of a ruptured aneurysm has a high risk (40 to 50 percent) of perioperative mortality. Elective aneurysm repair, by contrast, has an associated mortality risk of 1 to 5 percent. Up to 5096 of patients with untreated aneurysms die of rupture in a 5-year period.

Medical therapy for abdominal aortic aneurysms is thought to be ineffective in preventing rupture. For the past 40 years, the standard treatment for abdominal aortic aneurysm has remained relatively unchanged: open abdominal repair. Open repair is contraindicated in many patients, usually because of advanced age and associated medical problems.

For open abdominal repair, the surgeon makes a large midline incision (8 to 10 inches) exposing the entire abdominal cavity, including the aorta and other organs. The bowel is retracted from the operative field and the aorta is visually examined to determine the proper size and configuration of the synthetic graft that will be used to replace the diseased vessel. If the iliacs are involved or if there is not an adequate amount of healthy aorta distal to the graft, then a bifurcated graft is utilized. The aorta or the aorta and iliacs are cross-clamped proximal and distal to the aneurysm for a period of 30 to 90 minutes and the diseased section is replaced by a prosthetic graft by suture. The wall of the aorta is wrapped and sewn around the graft to protect it. The incision site is then closed with sutures and staples.

The open surgery procedure can take up to four hours to perform and has significant morbidity rates in 15 to 30 percent of patients. The average hospital stay associated with open abdominal repair is seven to twelve days, including time spent in the ICU. Patient recovery time can last three months. Mortality rates for the surgical repair of non-ruptured aneurysms from multicenter reports have a range of 3–5% and at approximately 7% in population based studies.

In recent years, a less invasive approach for repairing abdominal aortic aneurysms has been developed: endovascular repair. An endovascular graft procedure provides essentially the same treatment as open abdominal repair, but via a different access route. The surgeon begins by making small incisions above the femoral arteries in the groin area of each leg. Using catheters, the interventional physician then inserts the stent graft through the femoral artery and precisely places the graft at the appropriate anatomical location. The graft is secured into place by the self-expansion of the nitinol stent rings. This seals off the distended portion of the aorta from circulation.

The first commercially available endoluminal graft was implanted in the early 1990s. This early tube graft was applicable to only 5 to 10 percent of patients with abdominal aortic aneurysm due to anatomical considerations. Subsequent technological innovations have included the development of a bifurcated stent graft and improvements in delivery systems, which expand applicability to 40 percent of patients with abdominal aortic aneurysm.

The placement of endoluminal grafts generally has required a team approach, the team may include a cardiologist, surgeon, radiologist, and support staff. More extensive pre-case evaluation is required than with open surgical repair due to necessary considerations such as endovascular access, implantation sites and morphology of the aneurysm. Proper patient selection and customization of the endoluminal graft require careful pre-procedural imaging to address these anatomical requirements. In addition, the surgeon must be trained in the use of guidewires, catheters and imaging modalities.

Compared to open surgery, the endovascular procedure provides substantial patient benefits such as reduced trauma from the surgery, shorter hospital stay, shorter intensive care unit stay, less blood loss, and fewer postoperative complications such as pulmonary compromise.

One problem with presently available stent/stent graft systems lies in the delivery and deployment of the stent/stent graft. Typically a series of interfitting catheters and tubes are provided to push or otherwise move the stent graft from the catheter and allow it to be deployed. In practice, the use of such a "push-pull" type system is less than ideal. Physicians have indicated a better delivery and deployment approach would be desired.

Recently, Fiedler in U.S. Pat. Nos. 5,817,101 and 6,056,759 and Monroe in U.S. Pat. No. 6,113,608 have proposed hydraulically operated systems to be used in deploying a stent. Both are complex in construction and include numerous pieces, further they present a multi piece large diameter short stent/stent-graft containment sheath that is not well adapted for the needs of insertion of a stent graft placement system which requires the ability to release with smooth reliability without kinking and without binding.

SUMMARY OF THE INVENTION

The present invention addresses the problems relating to stent delivery and deployment through the use of a retraction section, which permits the use of at least two different materials to be used for the stent containment portion and the stent retraction section of the stent containment sheath of a stent/stent-graft delivery system. Further, when using a stent retraction section for the efficient retraction of the containment sheath an anti kinking spacer is used to prevent the surrounding containment sheath from kinking and binding. The anti kinking spacer can be made of a weak closely wound helical spring and alternatively the cross section of individual windings of the spring can be tapered to be thick near the central axis and thinner near the perimeter edge. Moreover, a device according to the invention uses fluid pressure within a catheter to retract a stent graft containment sheath to thereby allow the delivery of a stent graft.

BRIEF DESCRIPTION OF THE DRAWINGS

FIG. 1 is a view of a stent graft system according to the present invention in which the stent graft is not deployed;

FIG. 2 is a view of a stent graft system according to the present invention in which the stent graft is deployed;

FIG. 3 is a cross sectional view of a stent containment sheath according to the invention and items contained therein in when the stent graft is contained therein;

FIG. 4 is a cross sectional view of a stent containment sheath according to the invention and items contained therein in when the stent graft has been deployed there around;

FIG. 5 is a cross sectional view of a stent containment sheath similar to that shown in FIG. 4, where the stent containment portion of the stent containment sheath has a larger diameter and a thinner wall thickness than the stent retraction section of the stent containment sheath;

FIG. 6 shows a side cross sectional view of the stent containment sheath of a stent delivery system where a bend in the delivery system occurs near the location of the stent retraction section of the stent containment sheath;

FIG. 7 shows a perspective view of short section of an anti kink spacer according to the invention having a substantially rectangular winding cross section;

FIG. 7A shows a cross sectional view of the antikinking spacer as shown in FIG. 7 with the contact between adjacent windings due to the bending around a curve taking place at the inside of the bend;

FIG. 8 shows a cross sectional view of an anti kinking spacer according to the invention having substantially planar windings whose thickness tapers from a larger thickness near a central axis of the spacer to a smaller taper as the distance from the central axis of the taper increases, the contact point between adjacent windings when the spacer is curved around a bend is at the inside of the curve formed by adjacent contact points of the large thickness of the tapering thickness of the winding;

FIG. 9A shows a cross sectional view of a portion of the stent containment sheath wherein the stent containment section and the stent retraction section of the sheath are of substantially the same diameter, and wall thickness, and are composed of different materials, while FIG. 9B shows different diameters, wall thicknesses, and materials for a second embodiment of a stent containment sheath according to the invention;

FIGS. 10A and 10B show plan views of the catheter sections associated with the stent containment sheaths shown in FIGS. 9A and 9B and which would be contained within a portion of such sheaths during insertion and deployment;

FIG. 11 shows a cross sectional end view of a stent delivery system according to the invention taken at 11—11 of FIG. 4;

FIG. 12 shows a cross sectional end view of a stent delivery system according to the invention taken at 12—12 of FIG. 4; and FIG. 13 is an alternate embodiment of the cross sectional end view of FIG. 12, showing an alternate arrangement of catheter lumens for use in a stent delivery system according to the invention.

The Figures are not necessarily to scale.

DETAILED DESCRIPTION

FIG. 1 is a view of a stent graft system according to the present invention in which the stent graft is not deployed. As seen the system 30 features a source of pressurized fluid, such as a syringe 32, coupled to the catheter body 34 through a Y-type fitting 38. As seen, the catheter body 34 is used typically over a guidewire 40. The guidewire 40, however, may not always be needed or desired to use the system shown. The distal section 42 of catheter body 34 features a backstop 50. The backstop 50 is fixed to the catheter body 34 so as to limit travel of the containment sheath 52. As seen, containment sheath 52 is positioned about and towards the distal end 42 of the catheter body 34. At the proximal end of containment sheath is proximal taper 54. Proximal taper 54 permits the relatively larger diameter containment sheath to be moved within a patient's body, while minimizing the likelihood of sharp edges catching and damaging tissue. Proximal taper 54 further is designed so as to be able to engage against backstop 50, so as to thereby limit the further proximal movement of containment sheath 52, as will be described below. Positioned distal to the containment sheath 52 is distal nose 56. The distal nose 56 is fixed to the catheter body 34 and functions to act as the distal cover of the distal edge of containment sheath 52. Like the proximal taper 54, the distal nose 56 also permits the relatively larger diameter containment sheath to be moved within a patient's body, while minimizing the likelihood of sharp edges catching and damaging tissue.

FIG. 2 is a view of a stent graft system of FIG. 1, in which the stent graft has been deployed. The syringe plunger has been depressed so as to force fluid from the syringe into the catheter and into a fluid delivery chamber (described in detail below). Such an introduction of fluid, under sufficient pressure, causes the containment sheath 52 to move proximally, in proximal direction shown by the arrow 64, so as to ultimately abut against backstop 50. This movement causes the lumen of the containment sheath 52 to no longer contain a stent graft 60 formerly contained therein. The containment sheath 52 is moved to a location equal to or beyond the stent cup plunger 66. Stent cup plunger 66 is a ring type structure engaged with the catheter body 34 and is sized to snugly fit within the containment sheath 52 wherein the stent cup plunger 52 acts as the end surface of the anti kink spacer which as the spacer coils are compressed and contact one another and become inflexible establishes a limit for the movement in the proximal direction by the stent graft 60 as the containment sheath 52 is moved in the proximal direction 64.

Stent graft 60 discussed may be any self expanding stent or stent graft sized to be released from a complimentarily sized containment sheath, although in one embodiment the stent graft comprises a Talent>> stent graft, available from Medtronic AVE, Sunrise, Fla., a division of Medtronic AVE, Santa Rosa, Calif.

Pressurized fluid directed toward a fluid receiving chamber within a system of fluid seals between the containment sheath 52 and the catheter 34 is used to move the containment sheath 52 in the proximal direction 64. The pressurization limits of the fluid receiving chamber are described below.

FIG. 3 is a detailed sectional view of the distal end of the stent graft system showing the contents of the containment sheath 52 of the stent graft system 30 which includes the fluid receiving chamber.

The containment sheath 52 and proximal taper 54 have a movable seal mount 71 fixed thereto. The moveable seal mount 71 including an end wall and series of two peripheral ridges configured and sized in this embodiment to mount, receive, and retain two side by side O-rings which form the second or movable fluid seals 70. The fluid seals as described therein can also be lip seals or other seal configurations compatible with sealing between substantially circular cylinders as the catheter 34 outer surface and the inner surface of the fluid receiving chamber and a sheath retraction section 80 inner surface of the containment sheath 52. The movable seal mount 71 causes the O-rings of the movable seal 71 to move with the containment sheath 52 as it moves along the catheter 34 when the fluid receiving chamber is pressurized. The movable fluid seals 70 are dimensioned to provide a fluid tight seal with catheter body 34 while still permitting sliding movement with respect to the catheter body 34.

Similarly the catheter body 34 has a set of fixed (first) fluid seals 72 fixed to a fixed seal mount 73; where the fixed fluid seals 72 provide a fluid tight seal with the inside surface of the containment sheath 52 while still permitting sliding movement with the catheter body 34. The movable and fixed fluid seals 70, 72 define a fluid receiving chamber 75 therebetween. Located between the movable 70 and fixed 71 seals within fluid receiving chamber 22 is a fluid opening 76. Because the fixed fluid seals 72 are fixed to the catheter body 34 and the movable fluid seals 70 are fixed to the containment sheath 52/proximal taper 54, introducing pressurized fluid into the fluid receiving chamber 75 will cause the containment sheath 52 in this configuration to travel proximally (in a first direction) along the catheter body 34 (the first direction, for example as shown in the description of prior art patents). Such travel will continue so long as pressurized fluid continues to be introduced until such time as the proximal taper 54 reaches and abuts against backstop 50. At such time interference between the proximal taper 54 and the backstop 50 will permit no further travel. This is useful since through such a configuration the backstop may ensure that the fluid receiving chamber 75, which receives pressurized fluid, will not be exposed to body tissues directly. That is the pressurized fluid within fluid receiving chamber 75 will not be exposed to body tissues directly. Thus it is preferred that the backstop 50 be positioned along catheter body 34 so as to limit the proximal movement of containment sheath 52 such that fluid within the fluid receiving chamber will not be exposed to body tissue, while permitting sufficient movement such that the containment sheath 52 moves to permit full deployment of the stent graft 60.

The containment sheath can be configured with a continuous single diameter from end to end. However, the material of the sheath can be different in different sections of the sheath. A stent retention portion of the sheath adjacent to the compressed stent retention section 78 is constructed of a material having a lubricious inner surface having a low coefficient of friction so the stent graft 60 contained therein slides easily out during deployment as the sheath 52 is retracted. The material of the stent retention portion of the sheath 52 having the desired frictional qualities has been generally found to be soft and susceptible to scoring and the creation of surface irregularities as the containment sheath 52 is retracted and the stent graft 60 is deployed. If the scoring and other surface defects on the inside surface of the stent retention portion of the containment sheath 52 were to reach the location of the fixed seal 72 of the catheter 34, then the scoring and other surface irregularities on the inner surface of the sheath would create a leakage path a for the fluid being contained by the seal and the seal would leak. Therefore, an intermediate section identified as a stent retraction portion of the containment sheath 52 (initially positioned adjacent to a sheath retraction section 80 of the catheter body 34 is made of a material whose surface is less susceptible to scoring and the introduction of other surface defects than the softer surface finish material of the stent retention portion of the sheath. If the catheter was kept straight then the presence of the sheath retraction portion of the catheter would assure that the inside surface of the stent retention portion which may be scored or have other surface defects as a result of its contact and rubbing against the self expanding stent graft, can never occur. During deployment the stent cup plunger 66 acts as the end of a block (anchored by the fixed seal mount 73 through the anti kinking spacer) which prevents the stent graft 60 from moving proximally. However, if the distal portion of the stent graft assembly were severely bent prior to or during deployment of the stent graft, it is possible that the unreinforced tubular wall structure of the stent retraction portion of the containment sheath 52, corresponding to the sheath retraction section 80 of the catheter body 34, may buckle or kink. Such a buckling or kinking could create surface irregularities due to the migration of material were plastic deformation to occur, even if the catheter was to subsequently be straightened out. Further, if the buckled or kinked area was present during deployment, the narrowed diameter of the containment sheath at that point would create binding between the containment sheath 52 and the fixed seal structure, which would make it difficult if not impossible to further retract the sheath. To reduce or completely eliminate the possibility of such buckling or kinking an anti-kinking spacer 82 is provided around the sheath retraction section 80 of the catheter body 34 and within the stent retraction portion of the containment sheath 52 to maintain the radial spacing between the two. The anti-kinking spacer 82 is in one embodiment a weak helical spring having the weak axial qualities similar to the well known children's toy known as a Slinky.RTM. (e.g., as shown in FIG. 7). While not preferred, it simply could be a thick cross section helical spring. Another configuration of the spacer is shown in FIG. 8, where the cross sectional thickness of the individual windings is a tapered section 84, where the thickness closer to the central axis of the spacer is a thicker portion 85 that tapers to with a thinner portion 86 farther away from the central axis of the spacer. As can be seen in FIG. 11, the gap between the inside of the containment sheath 52 and the radial edge of the spacer 82 is about 0.030–0.040" (0.762–1.016 mm), however since the spacer is weak and flexible this radial gap may be considered a total radial gap which varies between the inside the outside edge of the spacer in the radial direction (the inside edge gap being between the catheter body 34 and the inside edge of the spacer. The diameter of the catheter is typically 7 French, while the diameter of the containment section is in the range of 18–25 French. The spacer can also be a stack of washers which are loosely positioned around the sheath retraction section 80 of the catheter body 34, or the spacer can be a series of washer like or helical ribs in a flexible liner material, such as an annular bellows structure, but without the requirement of pressure containment, though a pressurized annular structure might also be used, but would not provide the assurance of kink resistance that washer and helical structures do.

FIG. 4 shows the stent graft 60 of FIG. 3 with the containment sheath 52 in a fully retracted position. The proximal edge of stent containment portion of the containment sheath 52 has reached the location of the stent cup plunger 66, but has not been retracted by it so that the anti kink spacer 82 (which be made of an injection molded polymer rather that a metal as would usually be expected) is directly exposed to the deployment surroundings. This prevents dislodgment of the spacer and exposure of the edges of the stent cup plunger 66 to the surrounding tissue, which could act as a scraping surface were they to be exposed. The containment sheath 52 is fully retracted into interference with the backstop 50. Cross sections 11—11 and 12—12 are taken through the fluid receiving opening and the anti kinking spacer 82 shown here.

FIG. 5 is an alternate embodiment according to the invention having a containment sheath 53 where the diameter of the retraction portion surrounding the antikinking spacer 82 and the fluid receiving chamber section 74 are a smaller diameter (e.g., 10–12 Fr) to more maneuverable during insertion and positioning and removal, while the stent retention portion of the containment section is larger to contain the stent graft 61. The fluid receiving chamber section 74 has minimum extension length before deployment has begun, and has a nearly maximum extension length when once the stent or stent graft has deployed and has separated from the catheter and containment sheath portions of the delivery assembly. In this configuration the size of the stent cup plunger 67, needs to match the size of the stent containment portion of the larger diameter section 97 of the two diameter stent containment portion 53.

FIG. 6 shows a curved configuration of the stent graft delivery assembly of FIG. 3. Is this Figure the anti kinking function of an anti kinking spacer 83 with tapered windings can clearly be seen. The wall of the containment sheath is maintained in a smooth non buckling (kinking) transition. FIG. 8 provides a close up view of the usefulness of the tapered winding sections, where as the structure bends along the central axis the gaps between adjacent outer radial edges at the inside of the bend are diminished while the gaps between windings at the outer radial gap at the outside of the bend are increased. This configuration generally maintains the axial length of the spacer close to the central axis of the catheter, so that less gaps (sloppiness, spacing) are required between the anti kink spacer and its surround chamber, which reduces the likelihood that kinking will occur in these gaps.

FIGS. 7 and 7A show a partial side view and a cross sectional view of a helical (Slinky® like) anti kinking spacer as pictured in FIG. 3. As can be seen the stacked windings surrounding the catheter body, must separate to create a pivot point (between each of two adjacent windings) at the inside of the bend in this curve configuration. Thus the surrounding chamber (sheath retraction portion of the containment sheath) must always be sized long enough to accommodate the increased length of the outside diameter of the bend without binding at the ends and displacing and distorting the stent cup plungers 66, 67 or fixed seal mount 73.

In comparison the tapered winding configuration of the anti kinking member shown in FIG. 8, requires a smaller increase in the outer circumferential length than for the configuration shown in FIG. 7, as the pivot point for bends is located closer to the center of the catheter.

FIGS. 9A and 9B show the partial cross section of two alternative constructions of a containment sheath according to the invention. A first material section 98 having friction reducing qualities (such as PEBAX) for the easy release of a spring loaded (self expanding) stent graft contained therein is fixed through a fused joint 95 to a second more rigid material section 96 whose material qualities are chosen to maintain rigidity (e.g., PE) and the sealing of the fluid receiving chamber 75. In the configuration of FIG. 9B similarly a first material section 97 has increased lubricity on its inner surface, while a second material section 99 has structural properties compatible with use as walls of pressurized chambers and for maintaining seal integrity. The change in diameters shown in FIG. 9B is done through a transition section 101 with a joint 100 between the two material section, though the transition section could be a third material. In the construction of this configuration a standard sized catheter could be used all the way to the location of the joint, before the transition to a larger size is attached, reducing the need for specialized structures. Further as shown the thickness of the two section can be varied according the structural requirements, e.g., the stent containing portion 97 has a thinner wall than the second material retraction section 99.

FIGS. 10A and 10B show side views of a portion of the distal section of the catheter body as shown in the previous Figures. FIG. 10A pictures a configuration used in a uniform diameter configuration such as shown in FIG. 9A. The catheter includes the distal nose 56, the compressed stent retention section 78, the stent cup plunger 66 engaged on it, the sheath retraction section 80, the fixed seal mount 73 (including a seal limit plate with two adjacent grooves for O-ring retention), and a fluid opening 76. The catheter configured for use with the dual diameter sheath configuration of FIG. 9B includes the distal nose 57, the compressed stent retention section 79, the stent cup plunger 67 engaged on it, the sheath retraction section 81, the fixed seal mount 73 , and a fluid opening 76.

FIG. 11, as briefly discussed above, also show a guidewire lumen 90 and a fluid pressurizing lumen 92 in the catheter body.

FIG. 12 shows a cross section of the fluid pressurizing lumen 92 at the location of the fluid opening 76 which releases fluid into the fluid receiving chamber shown around the catheter 34.

FIG. 13 shows an alternate embodiment of a lumen arrangement in the catheter 34. A guidewire lumen 91 is centralized, within annular space acting as a fluid pressurizing lumen 93 to provide release of fluid into the fluid receiving chamber 75 through the fluid opening 77.

An embodiment of the invention includes a method for hydraulically retracting a stent containment sheath comprising the steps of: providing a catheter having fixed seal fixed to a fixed seal mount thereon, with a fluid receiving chamber section on one side of the fixed seal and an anti kinking spacer on a second side of the with a plunger cup disposed at the end of the antikinking spacer opposite the fixed seal with a stent in a compressed pre deployment position disposed around a stent retention section of the catheter beyond the plunger cup; surrounding a portion of a distal end of the catheter with a containment sheath such sheath containing the fixed seal and the fixed seal mount and the antikinking spacer and the plunger cup and the stent in the pre deployment position, the containment sheath being sized to seal against the fixed seal of the catheter and including a movable seal which moves with the containment catheter and seals against the catheter to establish a fluid receiving chamber between the catheter, the containment sheath and the fixed seal and the movable seal; and injecting fluid into a lumen of the catheter in communication with a fluid opening in the fluid receiving chamber, such pressurization causing the retraction sheath to retract with respect to the catheter and uncover the stent for deployment. The method further includes constructing the stent containment from at least two different diameters and/or materials (with respect to sliding friction or lubricity).

While the present invention has been described in detail with particular reference to specific embodiments, persons knowledgeable about the field of the invention will understand that variations and modifications can be made without departing from the spirit and scope of the invention.

The invention claimed is:

1. A stent delivery system comprising:
a stent having a compressed stent length;
a catheter having a guidewire lumen at least partially therethrough, and having a fluid pressurizing lumen therein separate from said guidewire lumen, said fluid pressurizing lumen extending between a proximal end thereof and a fluid opening at a distal end of said catheter;
said catheter having a compressed stent retention section which extends at least said compressed stent length in a first direction along said catheter from a stent plunger engaged with said catheter at a location near a distal end of said catheter, said catheter having a sheath retraction section which extends from said stent plunger for at least said compressed stent length in a second direction, which is opposite said first direction, to a fixed seal mount fixed to said catheter, said catheter further containing a fluid receiving chamber section containing said fluid opening, said fluid receiving chamber section extends from said fixed seal mount in said second direction for at least said compressed stent length to a maximum fluid receiving chamber extension length;
a stent containment sheath having a movable seal mount near a proximal end thereof, wherein said stent containment sheath in a pre stent deployment position is positioned surrounding a portion of a distal end of said catheter including said compressed stent retention section, said stent plunger, said sheath retraction section, said fixed seal mount, and a minimum fluid receiving chamber extension length, wherein said stent containment sheath in a post stent deployment position is positioned surrounding a portion of a distal end of said catheter including said stent plunger, said sheath retraction section, said fixed seal mount, and a substantial portion of said maximum fluid receiving chamber extension length,
wherein a stent retention portion of said stent containment sheath has an inner surface exposed to a stent containment sheath lumen made of a first material having a lubricious surface quality suitable for easy release of said stent contained therein, said sheath stent retention portion being of the same length as said catheter compressed stent retention section and in said pre stent deployment position extending in said first direction for at least said compressed stent length from said stent plunger,
wherein a stent retraction portion of said stent containment sheath is made of a second material different from said first material against which a first flexible seal structure of a fluid receiving chamber seals, said stent retraction portion of said sheath being of the same length as said catheter sheath retraction section and in said pre stent deployment position extending in said second direction for at least said compressed stent length from said stent plunger, wherein in the post stent deployment position said entire stent retention portion of said sheath remains distal of said fixed seal mount;
wherein said first flexible seal structure is disposed engaged with said fixed seal mount to flexibly seal between said catheter and said stent containment sheath at a first end of said fluid receiving chamber, said first flexible seal structure maintains engagement with said fixed seal mount as said fluid receiving chamber is pressurized and said stent containment sheath moves with respect to said catheter; and
a second flexible seal structure disposed engaged with said movable seal mount and flexibly sealing between said catheter and said stent containment sheath at an end opposite said first end of said fluid receiving chamber section and maintaining engagement with said movable seal mount as said fluid receiving chamber is pressurized and said stent containment sheath moves with respect to said catheter.

2. A stent delivery system comprising:
a catheter having a guidewire lumen at least partially therethrough, and having a fluid pressurizing lumen therein separate from said guidewire lumen, said fluid pressurizing lumen extending between a proximal end thereof and a fluid opening at a distal end of said catheter;
said catheter having a compressed stent retention section which extends at least a compressed stent length in a first direction along said catheter from a stent plunger engaged with said catheter at a location near a distal end of said catheter, said catheter having a sheath retraction section which extends from said stent plunger in a second direction which is opposite said first direction to a fixed seal mount fixed to said catheter, said catheter further containing a fluid receiving chamber section containing said fluid opening, said fluid receiving chamber section extends from said fixed seal mount in said second direction to a maximum fluid receiving chamber extension length;

a stent containment sheath having a movable seal mount near an end thereof, wherein said stent containment sheath in a pre stent deployment position is positioned surrounding a portion of a distal end of said catheter including said compressed stent retention section, said stent plunger, said sheath retraction section, said fixed seal mount, and a minimum fluid receiving chamber extension length, wherein said stent containment sheath in a post stent deployment position is positioned surrounding a portion of a distal end of said catheter including said stent plunger, said sheath retraction section, said fixed seal mount, and a substantial portion of said maximum fluid receiving chamber extension length, wherein a stent retention portion of said stent containment sheath is made of a first material having a lubricious inner surface suitable for easy release of a stent contained therein, wherein a stent retraction portion of said stent containment sheath is made of a second material having a smooth inner surface against which a first flexible seal structure of a fluid receiving chamber seals;

wherein said first flexible seal structure is disposed engaged with said fixed seal mount to flexibly seal between said catheter and said stent containment sheath at a first end of said fluid receiving chamber, said first flexible seal structure maintains engagement with said fixed seal mount as said fluid receiving chamber is pressurized and said stent containment sheath moves with respect to said catheter; and a second flexible seal structure disposed engaged with said movable seal mount and flexibly sealing between said catheter and said stent containment sheath at an end opposite said first end of said fluid receiving chamber section and maintaining engagement with said movable seal mount as said fluid receiving chamber is pressurized and said stent containment sheath moves with respect to said catheter, and an anti-kinking spacer loosely contained within said stent containment sheath and outside said sheath retraction section of said catheter and extending substantially between ends of said sheath retraction section and sized to substantially interfere with the linking of said stent containment sheath at a location adjacent to said anti-kinking spacer when said stent containment sheath containing a portion of said catheter is bent.

3. A stent delivery system as in claim 2, wherein said anti-kinking spacer is a helical spring.

4. A stent delivery system as in claim 3, wherein said anti-kinking spacer is a helical spring having a substantially planar coil shape.

5. A stent delivery system as in claim 4, wherein said anti-kinking spacer is a helical spring having a substantially planar coil shape whose thickness is larger near the central longitudinal axis of the helix and tapers to a smaller thickness near its outer edge.

6. A stent delivery system as in claim 2, wherein said anti-kinking spacer is a series of stacked rings.

7. A stent delivery system as in claims 2, 3, 4, 5, or 6, wherein an inside diameter of said stent containment sheath opposite said compressed stent retention section and the inside diameter of said stent containment sheath opposite said retraction section and said fluid receiving chamber are the substantially the same.

8. A stent delivery system as in claim 7, wherein said catheter has fixed to it a backstop which prevents fluid from being released from the fluid receiving chamber by the stent containment sheath moving so far with respect to the catheter that said fluid receiving chamber is no longer sealed by said first flexible seal structure.

9. A stent delivery system as in claim 2, 3, 4, 5, or 6, wherein an inside diameter of said stent containment sheath opposite said compressed stent retention section and the inside diameter of said stent containment sheath opposite said retraction section and said fluid receiving chamber are substantially different.

10. A stent delivery system as in claim 9, wherein said catheter has fixed to it a backstop which prevents fluid from being released from the fluid receiving chamber by the stent containment sheath moving so far with respect to the catheter that said fluid receiving chamber is no longer sealed by said first flexible seal structure.

11. A stent graft delivery system comprising:

a stent graft having a compressed stent graft length;

a catheter having a guidewire lumen at least partially therethrough, and having a fluid pressurizing lumen therein separate from said guidewire lumen, said fluid pressurizing lumen extending between a proximal end thereof and a fluid opening at a distal end of said catheter;

said catheter having a compressed stent graft retention section which extends at least said compressed stent graft length in a first direction along said catheter from a stent graft plunger engaged with said catheter at a location near a distal end of said catheter, said catheter having a sheath retraction section which extends for at least said compressed stent graft length from said stent graft plunger in a second direction, which is opposite said first direction, to a fixed seal mount fixed to said catheter, said catheter further containing a fluid receiving chamber section containing said fluid opening, said fluid receiving chamber section extends for at least said compressed stent graft length from said fixed seal mount in said second direction to a maximum fluid receiving chamber extension length;

a stent graft containment sheath having a movable seal mount near an end thereof, wherein said stent graft containment sheath in a pre stent graft deployment position is positioned surrounding a portion of a distal end of said catheter including said compressed stent graft retention section, said stent graft plunger, said sheath retraction section, said fixed seal mount, and a minimum fluid receiving chamber extension length, wherein said stent graft containment sheath in a post stent graft deployment position is positioned surrounding a portion of a distal end of said catheter including said stent graft plunger, said sheath retraction section, said fixed seal mount, and a substantial portion of said maximum fluid receiving chamber extension length, wherein a stent graft retention portion of said stent graft containment sheath has an inner surface exposed to a stent containment sheath lumen made of a first material having a lubricious surface quality suitable for easy release of said stent graft contained therein, said sheath stent graft retention portion being of the same length as said catheter compressed stent graft retention section and in said pre stent graft deployment position extending in said first direction for at least said compressed stent length from said stent graft plunger, wherein a stent graft retraction portion of said stent graft containment sheath is made of a second material different from said first material against which a first flexible seal structure of a fluid receiving chamber seals, said stent graft retraction portion of said sheath being of the same length as said catheter sheath retraction section and in said pre stent deployment position extending in said second direction for at least said compressed stent length from said stent graft plunger, wherein in the post stent graft deployment position said entire stent graft retention portion of said sheath remains distal of said fixed seal mount;

wherein said first flexible seal structure is disposed engaged with said fixed seal mount to flexibly seal between said catheter and said stent graft containment sheath at a first end of said fluid receiving chamber, said first flexible seal structure maintains engagement with said fixed seal mount as said fluid receiving chamber is pressurized and said stent graft containment sheath moves with respect to said catheter; and a second flexible seal structure disposed engaged with said movable seal mount and flexibly sealing between said catheter and said stent graft containment sheath at an end opposite said first end of said fluid receiving chamber section and maintaining engagement with said movable seal mount as said fluid receiving chamber is pressurized and said stent graft containment sheath moves with respect to said catheter.

12. The stent delivery system as in claim 1 or 11, wherein a wall thickness of said first material of said stent retention portion is different than a wall thickness of said second material of said stent retraction portion.

13. The system according to claim 11, wherein said stent graft is a self-expanding stent graft.

14. A stent graft delivery system comprising:

a catheter having a guidewire lumen at least partially therethrough, and having a fluid pressurizing lumen therein separate from said guidewire lumen, said fluid pressurizing lumen extending between a proximal end thereof and a fluid opening at a distal end of said catheter;

said catheter having a compressed stent graft retention section which extends at least a compressed stent graft length in a first direction along said catheter from a stent graft plunger engaged with said catheter at a location near a distal end of said catheter, said catheter having a sheath retraction section which extends from said stent graft plunger in a second direction which is opposite said first direction to a fixed seal mount fixed to said catheter, said catheter further containing a fluid receiving chamber section containing said fluid opening, said fluid receiving chamber section extends from said fixed seal mount in said second direction to a maximum fluid receiving chamber extension length;

a stent graft containment sheath having a movable seal mount near an end thereof, wherein said stent graft containment sheath in a pre stent graft deployment position is positioned surrounding a portion of a distal end of said catheter including said compressed stent graft retention section, said stent graft plunger, said sheath retraction section, said fixed seal mount, and a minimum fluid receiving chamber extension length, wherein said stent graft containment sheath in a post stent graft deployment position is positioned surrounding a portion of a distal end of said catheter including said stent graft plunger, said sheath retraction section, said fixed seal mount, and a substantial portion of said maximum fluid receiving chamber extension length, wherein a stent graft retention portion of said stent graft containment sheath is made of a first material having a lubricious inner surface suitable for easy release of a stent graft contained therein, wherein a stent graft retraction portion of said stent graft containment sheath is made of a second material having a smooth inner surface against which a first flexible seal structure of a fluid receiving chamber seals;

wherein said first flexible seal structure is disposed engaged with said fixed seal mount to flexibly seal between said catheter and said stent graft containment sheath at a first end of said fluid receiving chamber, said first flexible seal structure maintains engagement with said fixed seal mount as said fluid receiving chamber is pressurized and said stent graft containment sheath moves with respect to said catheter; and a second flexible seal structure disposed engaged with said movable seal mount and flexibly sealing between said catheter and said stent graft containment sheath at an end opposite said first end of said fluid receiving chamber section and maintaining engagement with said movable seal mount as said fluid receiving chamber is pressurized and said stent graft containment sheath moves with respect to said catheter, and an anti-kinking spacer loosely contained within said stent graft containment sheath and outside said sheath retraction section of said catheter and extending substantially between ends of said sheath retraction section and sized to substantially interfere with the kinking of said stent graft containment sheath at a location adjacent to said anti-kinking spacer when said stent graft containment sheath containing a portion of said catheter is bent.

15. A stent graft delivery system as in claim 14, wherein said anti-kinking spacer is a helical spring.

16. A stent graft delivery system as in claim 15, wherein said anti-kinking spacer is a helical spring having a substantially planar coil shape.

17. A stent graft delivery system as in claim 16, wherein said anti-kinking spacer is a helical spring having a substantially planar coil shape whose thickness is larger near the central longitudinal axis of the helix and tapers to a smaller thickness near its outer edge.

18. A stent graft delivery system as in claim 14, wherein said anti-kinking spacer is a series of stacked rings.

19. A stent graft delivery system as in claims 14, 15, 16, 17, or 18, wherein an inside diameter of said stent graft containment sheath opposite said compressed stent graft retention section and the inside diameter of said stent graft containment sheath opposite said retraction section and said fluid receiving chamber are the substantially the same.

20. A stent graft delivery system as in claim 19, wherein said catheter has fixed to it a backstop which prevents fluid from being released from the fluid receiving chamber by the stent graft containment sheath moving so far with respect to the catheter that said fluid receiving chamber is no longer sealed by said first flexible seal structure.

21. A stent graft delivery system as in claim 14, 15, 16, 17, or 18, wherein an inside diameter of said stent graft containment sheath opposite said compressed stent graft retention section and the inside diameter of said stent graft containment sheath opposite said retraction section and said fluid receiving chamber are substantially different.

22. A stent graft delivery system as in claim 21, wherein said catheter has fixed to it a backstop which prevents fluid from being released from the fluid receiving chamber by the stent graft containment sheath moving so far with respect to the catheter that said fluid receiving chamber is no longer sealed by said first flexible seal structure.

23. A stent delivery system comprising:
a catheter having a guidewire lumen at least partially therethrough, and having a fluid pressurizing lumen therein separate from said guidewire lumen, said fluid pressurizing lumen extending between a proximal end thereof and a fluid opening at a distal end of said catheter;
said catheter having a compressed stent retention section which extends at least a compressed stent length in a first direction along said catheter from a stent plunger engaged with said catheter at a location near a distal end of said catheter, said catheter having a sheath retraction section which extends from said stent plunger in a second direction which is opposite said first direction to a fixed seal mount fixed to said catheter, said catheter further containing a fluid receiving chamber section containing said fluid opening, said fluid receiving chamber section extends from said fixed seal mount in said second direction to a maximum fluid receiving chamber extension length;
a stent containment sheath having a movable seal mount near an end thereof, wherein said stent containment sheath in a pre stent deployment position is positioned surrounding a portion of a distal end of said catheter including said compressed stent retention section, said stent plunger, said sheath retraction section, said fixed seal mount, and a minimum fluid receiving chamber extension length, wherein said stent containment sheath in a post stent deployment position is positioned surrounding a portion of a distal end of said catheter including said stent plunger, said sheath retraction section, said fixed seal mount, and a substantial portion of said maximum fluid receiving chamber extension length;
a first flexible seal structure disposed engaged with said fixed seal mount and flexibly sealing between said catheter and said stent containment sheath at a first end of said fluid receiving chamber, said first flexible seal structure maintains engagement with said fixed seal mount as said fluid receiving chamber is pressurized and said stent containment sheath moves with respect to said catheter;
a second flexible seal structure disposed engaged with said movable seal mount and flexibly sealing between said catheter and said stent containment sheath at an end opposite said first end of said fluid receiving chamber section and maintaining engagement with said movable seal mount as said fluid receiving chamber is pressurized and said stent containment sheath moves with respect to said catheter; and,
an anti-kinking spacer loosely contained within said stent containment sheath and outside said sheath retraction section of said catheter and extending substantially between ends of said sheath retraction section and sized to substantially interfere with the kinking of said stent containment sheath at a location adjacent to said anti-kinking spacer when said stent containment sheath containing a portion of said catheter is bent.

24. A stent graft delivery system comprising:
a catheter having a guidewire lumen at least partially therethrough, and having a fluid pressurizing lumen therein separate from said guidewire lumen, said fluid pressurizing lumen extending between a proximal end thereof and a fluid opening at a distal end of said catheter;
said catheter having a compressed stent graft retention section which extends at least a compressed stent graft length in a first direction along said catheter from a stent graft plunger engaged with said catheter at a location near a distal end of said catheter, said catheter having a sheath retraction section which extends from said stent graft plunger in a second direction which is opposite said first direction to a fixed seal mount fixed to said catheter, said catheter further containing a fluid receiving chamber section containing said fluid opening, said fluid receiving chamber section extends from said fixed seal mount in said second direction to a maximum fluid receiving chamber extension length;
a stent graft containment sheath having a movable seal mount near an end thereof, wherein said stent graft containment sheath in a pre stent graft deployment position is positioned surrounding a portion of a distal end of said catheter including said compressed stent graft retention section, said stent graft plunger, said sheath retraction section, said fixed seal mount, and a minimum fluid receiving chamber extension length, wherein said stent graft containment sheath in a post stent graft deployment position is positioned surrounding a portion of a distal end of said catheter including said stent graft plunger, said sheath retraction section, said fixed seal mount, and a substantial portion of said maximum fluid receiving chamber extension length;
a first flexible seal structure disposed engaged with said fixed seal mount and flexibly sealing between said catheter and said stent graft containment sheath at a first end of said fluid receiving chamber, said first flexible seal structure maintains engagement with said fixed seal mount as said fluid receiving chamber is pressurized and said stent graft containment sheath moves with respect to said catheter;
a second flexible seal structure disposed engaged with said movable seal mount and flexibly sealing between said catheter and said stent graft containment sheath at an end opposite said first end of said fluid receiving chamber section and maintaining engagement with said movable seal mount as said fluid receiving chamber is pressurized and said stent graft containment sheath moves with respect to said catheter; and,
an anti-kinking spacer loosely contained within said stent graft containment sheath and outside said sheath retraction section of said catheter and extending substantially between ends of said sheath retraction section and sized to substantially interfere with the kinking of said stent graft containment sheath at a location adjacent to said anti-kinking spacer when said stent graft containment sheath containing a portion of said catheter is bent.

25. A method for hydraulically retracting a stent containment sheath comprising the steps of:
providing a catheter having fixed seal fixed to a fixed seal mount thereon, with a fluid receiving chamber section on one side of said fixed seal and an anti kinking spacer on a second side of said with a plunger disposed at the end of said anti-kinking spacer opposite the fixed seal with a stent in a compressed pre deployment position disposed around a stent retention section of the catheter beyond the plunger;
surrounding a portion of a distal end of said catheter with a containment sheath such sheath containing said fixed seal and said fixed seal mount and said antikinking spacer and said plunger and said stent in said pre deployment position, said containment sheath being sized to seal against said fixed seal of said catheter and including a movable seal which moves with the containment catheter and seals against said catheter to establish a fluid receiving chamber between the catheter, the containment sheath and the fixed seal and the movable seal; and injecting fluid into a lumen of said catheter in communication with a fluid opening in said fluid receiving chamber, such pressurization causing said retraction sheath to retract with respect to said catheter and uncover the stent for deployment.

26. The method of claims 25, wherein the stent containment sheath is constructed from at least two different diameter tubes.

27. The method of claim 25, wherein the stent containment sheath is constructed from at least two different materials having substantially different surface lubricity.

28. A stent delivery system comprising:
   a catheter having a guidewire lumen at least partially therethrough;
   said catheter having a compressed stent retention section which extends at least a compressed stent length in a first direction along said catheter from a stent plunger engaged with said catheter at a location near a distal end of said catheter, said catheter having a sheath retraction section which extends from said stent plunger in a second direction which is opposite said first direction;
   a stent containment sheath, wherein said stent containment sheath in a pre stent deployment position is positioned surrounding a portion of a distal end of said catheter including said compressed stent retention section, said stent plunger, and said sheath retraction section, and
   an anti-kinking spacer loosely contained within said stent containment sheath and around said sheath retraction section of said catheter and extending substantially between ends of said sheath retraction section and sized to substantially interfere with the kinking of said stent containment sheath at a location adjacent to said anti-kinking spacer when said stent containment sheath containing a portion of said catheter is bent, wherein said anti-kinking spacer is a helical spring having windings with substantially planar opposing surfaces, each winding having a tapered thickness from a larger thickness near a central longitudinal axis of the helix to a smaller thickness at an outer radial edge of the winding such that the windings have frustum-like cross-sections.

29. A stent delivery system as in claim 28, wherein when said anti-kinking spacer is unbent a distance between said substantially planar opposing surfaces of adjacent windings is greatest at said outer radial edges of said coils.

* * * * *

UNITED STATES PATENT AND TRADEMARK OFFICE
CERTIFICATE OF CORRECTION

PATENT NO.       : 7,163,552 B2
APPLICATION NO.  : 09/978243
DATED            : January 16, 2007
INVENTOR(S)      : Juan-Carlos Diaz Page 1 of 1

It is certified that error appears in the above-identified patent and that said Letters Patent is hereby corrected as shown below:

Column 11, line 44, "to substantialy interfere with the linking of said stent" should be changed to -- to substantially interfere with the kinking of said stent --

Signed and Sealed this

Twenty-third Day of October, 2007

JON W. DUDAS
*Director of the United States Patent and Trademark Office*